United States Patent [19]  [11] Patent Number: 4,591,247
Kamiya et al.  [45] Date of Patent: May 27, 1986

[54] EYE REFRACTOMETER

[75] Inventors: Minoru Kamiya; Masayuki Masuyama; Ikuo Kitao; Shinji Wada; Kiwami Horiguchi, all of Tokyo, Japan

[73] Assignee: Tokyo Kogaku Kikai Kabushiki Kaisha, Tokyo, Japan

[21] Appl. No.: 384,338

[22] Filed: Jun. 2, 1982

[30] Foreign Application Priority Data

Jun. 3, 1981 [JP] Japan ................................. 56-85489
Jul. 22, 1981 [JP] Japan ............................... 56-114933

[51] Int. Cl.⁴ .............................................. A61B 3/10
[52] U.S. Cl. .................................................. 351/211
[58] Field of Search ........................ 351/211, 205, 221

[56] References Cited

U.S. PATENT DOCUMENTS 3,614,214 10/1971 Cornsweet et al. ............ 351/211 X
4,173,398 11/1979 Okamoto ............................. 351/211
4,266,862 5/1981 Trotscher .............................. 351/211
4,293,198 10/1981 Kahayakawa et al. .............. 351/211
4,293,199 10/1981 Wada et al. ..................... 351/211 X
4,304,468 12/1981 Wada et al. ......................... 351/211
4,306,778 12/1981 Wada et al. ......................... 351/211
4,353,625 10/1982 Nohda et al. ....................... 351/211

Primary Examiner—Rodney B. Bovernick
Attorney, Agent, or Firm—Brumbaugh, Graves, Donohue & Raymond

[57] ABSTRACT

An eye refractometer comprising a measuring target projection optical system for projecting a measuring target image to the eye fundus of a patient's eye by means of a pair of beams of light from a measuring target; a rotating device for rotating the pair of beams of light around the optical axis; a measuring target image-forming optical system for forming a target image of the beams of light projected through the measuring target image projected to the eye fundus; a detection device for two-dimensionally detecting the position of the target image formed by the image-forming optical system on a plane perpendicular to the optical axis; and an operating circuit for obtaining a refractive power of the eye along a radial line passing through the centers of the pair of beams of light by means of the signal from the detection device.

6 Claims, 12 Drawing Figures

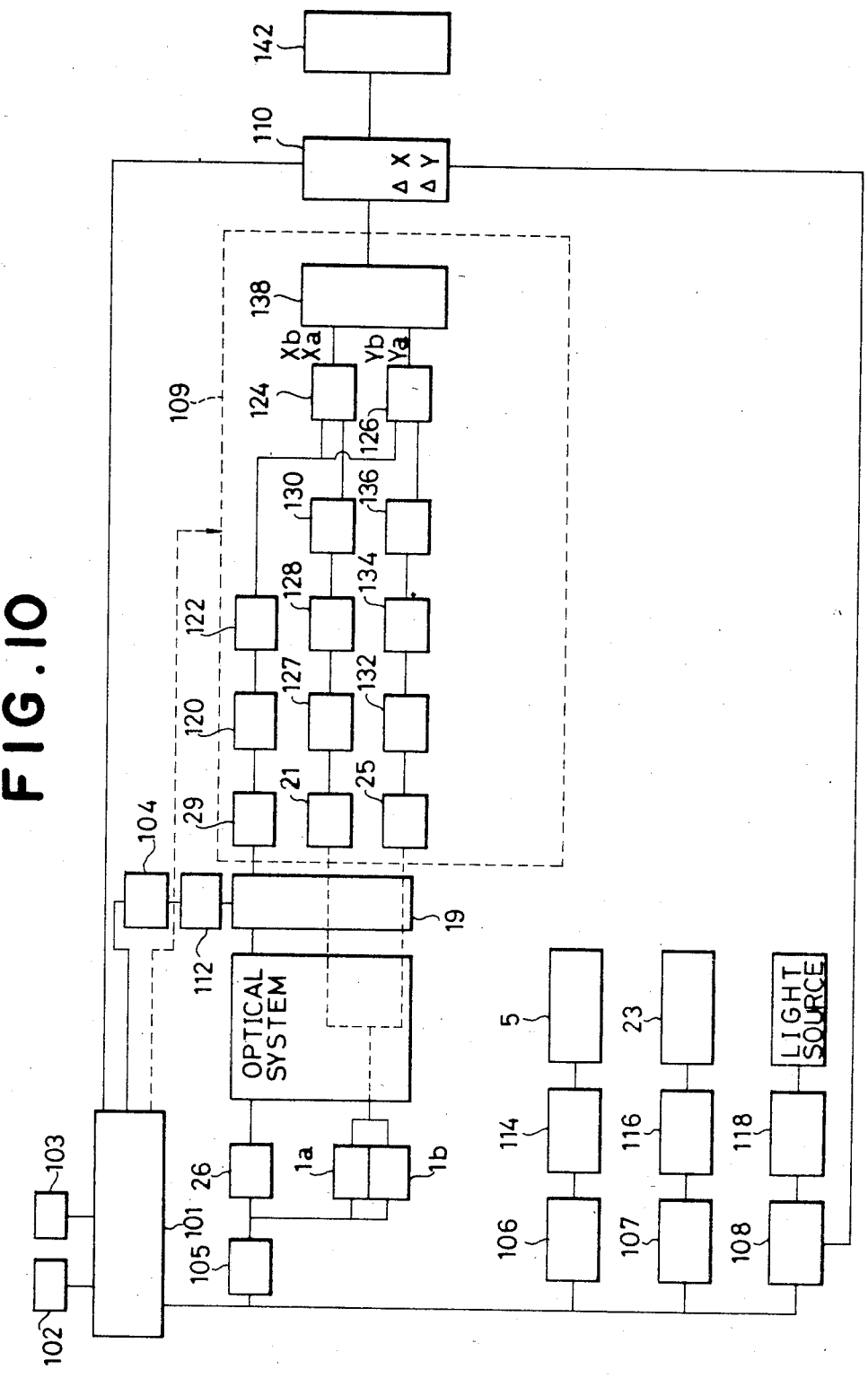

EYE REFRACTOMETER

BACKGROUND OF THE INVENTION

This invention relates to an eye refractometer for automatically measuring the refractive power of the eye.

As an example of the abovementioned eye refractometer, there is a known apparatus comprising a measuring target projection system including two light sources arranged at positions symmetric about an optical axis and a target moving on the optical axis and two light receiving elements arranged at positions conjugate with each other with respect to an objective lens and symmetric with respect to the optical axis. In this apparatus, the beams of light emitted from the two light sources, which are alternately lit, passes through the target at a certain angle relative to the optical axis and are projected onto the eye fundus. The refraction is calculated in terms of a quantity of movement of the target when the target is moved until the two target images of both beams of light on the eye fundus are formed at the same position and the amounts of light received by the two light receiving elements become equal to each other.

However, the conventional eye refractometer has the following two drawbacks. The first drawback is that the apparatus measures refraction in only the meridian direction including the optical axis and the two light sources. In order to measure the refraction in an other meridian direction, the two light sources as well as the two light receiving elements must be rotated through the same angle about the optical axis as the center. However, the construction of such an apparatus becomes complicated and it fails to provide a high level of accuracy because a large number of moving parts are necessary. In another type of an apparatus for measuring the refraction in a plurality of meridian directions, an image rotator is disposed inside a common optical path of the measuring target projection system including the two light sources and the target and a detecting optical system including the light receiving elements. When the image rotator is rotated, the same effect can be obtained as when both the measuring target projection system and detecting optical system are simultaneously rotated in the same direction by the same angle. In this kind of the apparatus, however, the image rotator becomes large and the optical length of each of the measuring target projection system and the detecting optical system must be elongated in order to permit the image rotator to be inserted, inviting difficulty in design. Moreover, a ghost flare is likely to occur because the image rotator includes a large number of reflecting surfaces.

The second drawback is that the measurement is very time consuming because the target must be moved on the optical axis to focus the target image on the eye fundus whenever the refraction is measured in each radial direction. This results not only in the fatigue of the patient but also in changes in the measuring conditions of the eye to be inspected during measurement so that measurement can not be done with a high level of accuracy.

As still another example of a conventional eye refractometer, an apparatus is also known which comprises the measuring target projection system including two light sources arranged at positions symmetric about an optical axis and the target fixed on the optical axis, a target image measuring system for measuring the distance between two target images on the eye fundus and an operation system for calculating the refraction from the distance measured by the target image measuring system. This apparatus has the problem that the measuring accuracy drops if the distance between the two target images becomes great, that is to say, the problem that the measuring range of the refraction becomes narrow.

SUMMARY OF THE INVENTION

It is an object of the present invention to provide an eye refractometer which can measure the refraction in an arbitrary meridian direction without rotating a measuring system for measuring the distance between the target images on the eye fundus about the optical axis as the center.

It is another object of the present invention to provide an eye refractometer which has a wide measuring range and provides a high level of measuring accuracy.

It is still another object of the present invention to provide an eye refractometer which can measure the spherical power, the cylindrical power, and the direction of the cylindrical axis of the eye within a short period of time.

According to the present invention, these and other objects can be accomplished by an eye refractometer comprising a measuring target projection optical system for projecting a measuring target image along an optical axis to the eye fundus of a patient's eye by means of a pair of beams of light from a measuring target; rotation means for rotating said pair of beams of light around the optical axis; a measuring target image-forming optical system for forming a target image of said beams of light projected through measuring target to the eye fundus; detection means for detecting position of the target image formed by said image-forming optical system on a plane perpendicular to the optical axis; and operating means for obtaining a refractive power of the eye along a radial line passing through centers of said pair of beams of light by means of signals from said detection means.

BRIEF DESCRIPTION OF THE DRAWINGS

FIG. 10 is a block diagram of the electric circuit in the embodiment of the present invention.

DESCRIPTION OF THE PREFERRED EMBODIMENT

Figure 1:
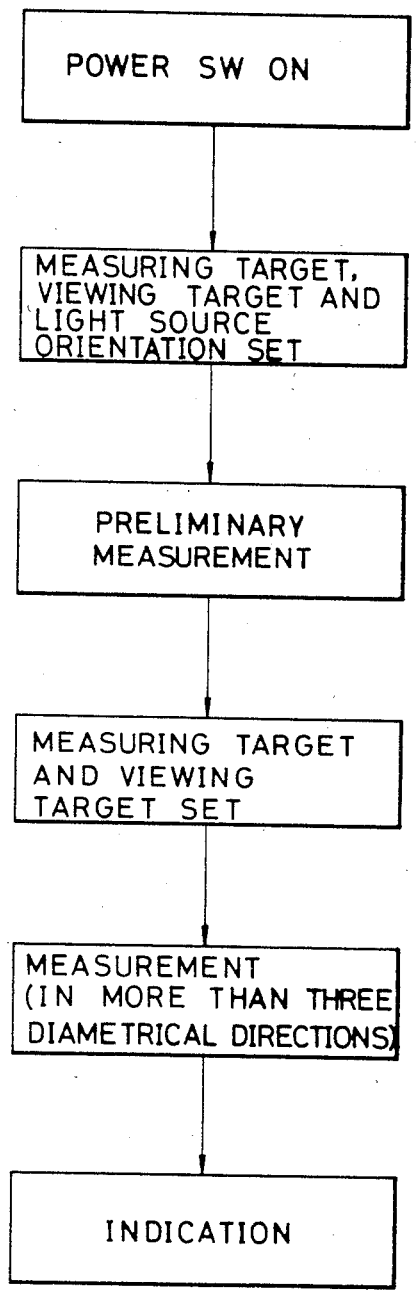
FIG. 1 is a diagram showing the measuring procedures in the embodiment of the present invention.

An embodiment of the present invention will now be described with reference to the accompanying drawings. First, the procedure of measuring with the apparatus in accordance with the embodiment of the invention will be explained with reference to FIG. 1. After the power switch is turned on, the measuring target and the fixed reference target are set to predetermined positions and the light source for the measuring target projection optical system is also set to a predetermined position of rotation. Preparatory measurement is carried out in this state and a rough spherical power is measured. Next, on the basis of the value measured in the preparatory measurement, the measuring target is moved to a position conjugate with the eye fundus of the patient's eye and fixed there while the fixed reference target is placed at a position remote from the measuring target and clouds the patient's eye. The real measurement is carried out in this state. This measurement is effected in at least three meridian directions while the light source for the measuring target projection optical system is rotated about the optical axis as the center. Next, the spherical power, the cylindrical power and the cylindrical axis are calculated from the measured values and the resulting values are displayed, thus finishing the measurement.

Figure 2:
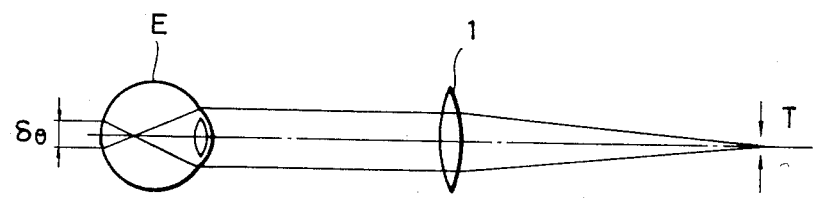
FIGS. 2 and 3 ae schematic views useful for explaining the principle of measurement of the embodiment of the present invention.

Next, the principle of calculating the refraction in a predetermined meridian direction will be explained. In FIG. 2, the amount of displacement $\delta_\theta$ of two beams of light, that are projected from the measuring target T in the separate arrangement to an arbitrary meridian direction of the pupil of the patient's eye E through the light transmitting objective lens 1, depends upon the index ametropia which is an anomaly of refraction of the crystalline lens of the patient's eye or upon axial ametropia of the patient's eye which is an abnormality of the distance from the crystalline lens to the eye fundus, but the angle $\beta_\theta$ defined by lines connecting the two deviated points on the eye fundus of the patient's eye resulting from the two beams of light is given by the following equation for both the index and axial ametropia:

$$\tan \beta_\theta = X(D^\theta - D_T) \qquad (1)$$

where
X: distance between two beams of light on the pupil of the subject eye
$D_\theta$: refraction of the patient's eye in the meridian direction $\theta$ on the pupil
$D_T$: diopter conversion value at the measuring target position.

Figure 3:
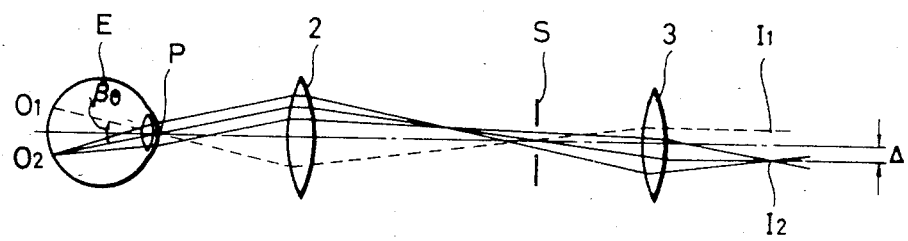

Accordingly, if an aperture S is disposed at a position conjugate with the pupil P of the patient's eye E by the light receiving objective lens 2 and at the forward focal point of a relay lens 3 in the optical system shown in FIG. 3, the reflected rays of light from the deviated positions $O_1$, $O_2$ on the eye fundus of the patient's eye can be picked up as beams of light of the principal rays of light passing through the center of the pupil P of the patient's eye. The angle defined by the two outgoing beams of light corresponds to the angle $\beta_\theta$ defined by the line connecting the center of the pupil P of the patient's eye to the points $O_1$, $O_2$ on the eye fundus. Here, if the image-forming magnification of the aperture S to the patient's eye P is m and the focal distance of the relay lens 3 is $f_3$, the rays of light reflected from the points $O_1$ and $O_2$ on the eye fundus of the patient's eye form an image outside the optical axis formed by the relay lens 3 and the image height $\Delta$ from the optical axis is given by:

$$\Delta = f_2 \tan m\beta\theta \qquad (2).$$

Incidentally, since the aperture S has the relation of a telecentric system with the relay lens 3, the image height $\Delta$ remains unchanged even in front of and behind the image-forming position of the relay lens 3. If $\beta_\theta$ is small and m=1, equation (2) can be changed as follows:

$$\Delta = mf_3 \tan \beta\theta \qquad (3).$$

From equation (1) and (3), $$\Delta = mf_3 X(D_{74} - D_T) \qquad (4).$$

Accordingly, the refraction $D_\theta$ of the patient's eye in the meridian direction $\theta$ can be calculated by measuring the image height $\Delta$ of the relay lens 3.

Figure 4:
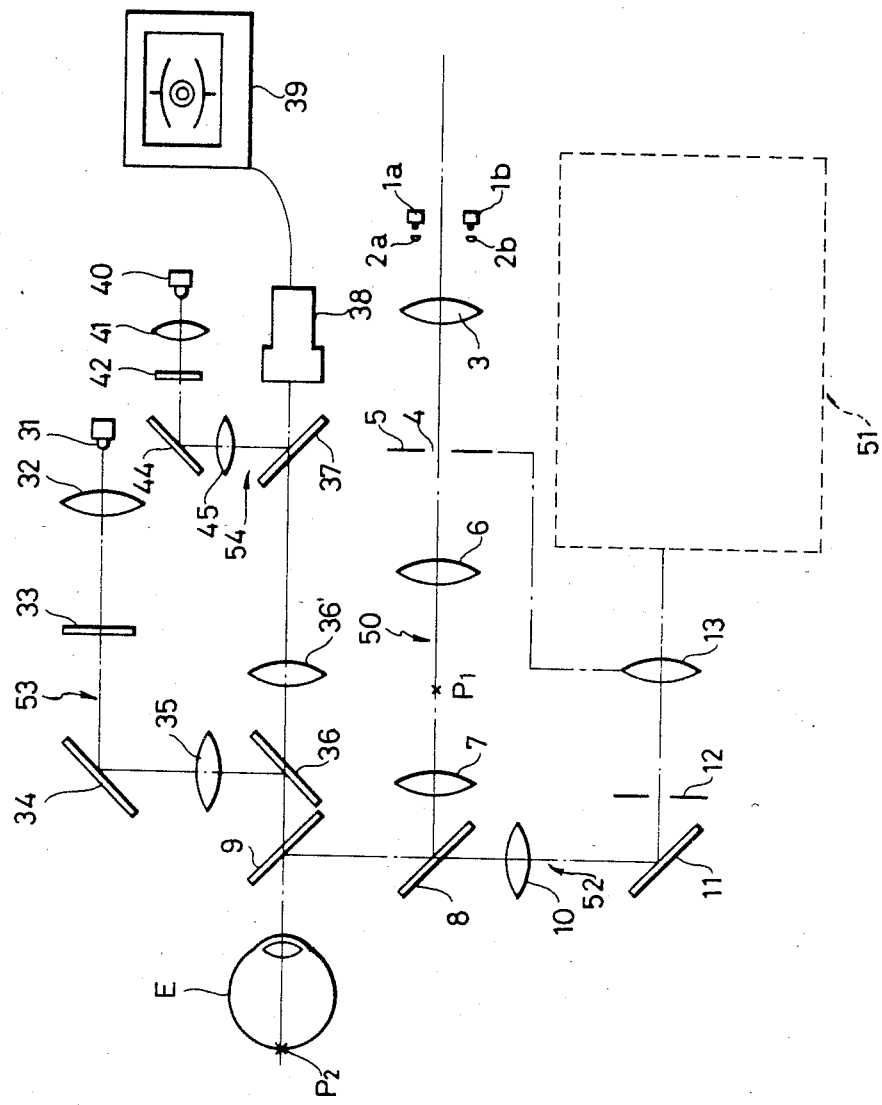
FIG. 4 is an optical diagram of the embodiment of the present invention.

FIG. 4 diagrammatically illustrates the eye refractometer in accordance with the embodiment of the present invention. The apparatus comprises the measuring target projection optical system 50 for projecting the measuring target onto the eye fundus of the patient's eye, the target light receiving optical system 52 for projecting the measuring target image projected on the eye fundus of the patient's eye into a measuring optical system 51, the measuring optical system 51 for detecting the refraction from the measuring target image, the fixed reference target system 53 for fixing the sight line of the patient's eye and an illumination optical system 54 for displaying the relationship between the positions of the patient's eye and the apparatus of the invention. Each optical system will be now explained in detail.

As illustrated in FIG. 4, the target projection optical system 50 consists of a pair or infrared light sources 1a and 1b disposed centered around the optical axis; condenser lenses 2a and 2b for condensing the rays of light from the infrared light sources 1a and 1b, respectively; a collimator lens 3 for forming a parallel pencil of rays; the measuring target 5 having a round aperture 4; an image-forming lens 6, an image-forming lens 7 for projection; a half mirror 8 associated with the infrared rays; and a dichroic mirror 9 having such properties as to reflect the long wave infrared rays and to permit the passage of the visible and near-visible infrared rays. The pair of infrared light sources 1a and 1b are alternately lit at a high speed and are rotatable integrally with each other with the condenser lenses 2a and 2b around the optical axis as the center, and the measuring target 5 can move in the direction of the optical axis.

In the abovementioned construction, the rays of light from the pair of infrared light sources 1a and 1b are condensed by the condenser lenses 2a and 2b, respectively, are converted into the parallel pencil of rays by the collimator lens 3 and are slantingly incident to the round aperture 4. After passing through the round aperture 4, the rays of light are made to form an image at the point $P_1$ by the image-forming lens 6 and are thereafter incident on the patient's eye E through the image-forming lens 7 for projection, the half mirror 8 and the dichroic mirror 9. Here, the image of the infrared light sources 1a and 1b forms the image at the position of the pupil of the patient's eye E and the image of the round aperture 4 of the measuring target 5 forms the image at the point $P_2$ of the eye fundus of the patient's eye. When the measuring target 5 and the eye fundus $P_2$ of the patient's eye have the conjugate relation of position, the image of the round aperture 4 illuminated by the rays of light from the infrared light source 1a and the image of the round aperture 4 illuminated by the rays of light from the infrared light source 1b are formed at the same position on the eye fundus $P_2$.

On the other hand, when the measuring target 5 and the eye fundus $P_2$ of the patient's eye do not have the conjugate relation, the images of the round aperture 4 illuminated by the infrared light sources are formed at two separate positions on the eye fundus $P_2$, respectively. In the present invention, it is identified whether the images of the round aperture 4 of the measuring target 5, which is fixed on the optical axis, on the eye fundus $P_2$ coincide with or are separate from eath other by alternately lighting the infrared light sources 1a and 1b. When the images are separate, the distance of separation is measured and the refraction of the patient's eye is calculated from the positions of the measuring apparatus and the measuring target at that time.

Figure 5:
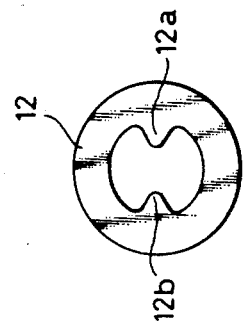
FIG. 5 is a front view of the corneal reflected light cut-off aperture.

As shown in FIG. 4, the target light receiving optical system 52 consists of the dichroic mirror 9; the half mirror 8; the light receiving objective lens 10; a mirror 11; a cut-off aperture 12 for cutting off the corneal reflected light which is arranged at a position conjugate with the cornea of the patient's eye with respect to the light receiving objective lens 10; and a relay lens 13. The cut-off aperture 12 for cutting off the corneal reflected light is a substantially round aperture plate equipped with projecting light-intercepting portions 12a and 12b at two positions symmetric with the position of the passage of the optical axis, as shown in FIG. 5. The cut-off aperture 12 is constructed such that it can rotate in an interlocking arrangement with the infrared light sources 1a, 1b and the condenser lenses 2a, 2b when they rotate around the optical axis. Furthermore, the cut-off aperture 12 is disposed behind the objective lens system at a position conjugate to the pupil of the eye and the projection optical system is constructed as a telecentric optical system. The relay lens 13 is movable in the direction of the optical axis in an interlocking arrangement with the measuring target 5.

In the abovementioned construction, the measuring target image of the eye fundus $P_2$ of the patient's eye is projected into the measuring optical system 51, which will be described in detail elsewhere, by the dichroic mirror 9, the half mirror 8, the light receiving objective lens 10, the mirror 11 and the relay lens 13. In this instance, the detrimental light reflected from the cornea of the patient's eye is removed by the projecting light intercepting portions 12a and 12b of the reflected light cut-off aperture 12. Since the corneal reflected light cut-off aperture 12 and the relay lens 13 together form a telecentric optical system, the measuring target image formed in the measuring optical system 51 is composed of the beams of light consisting of the main rays of light that are parallel to the optical axis and the center position of the round hole image as the measuring target image does not undergo displacement both in front and behind the image-forming position.

Figure 6:
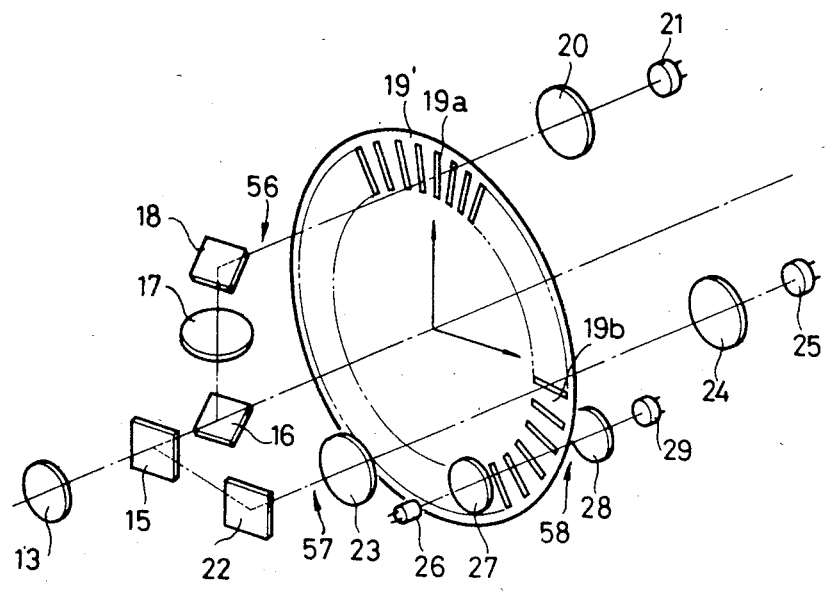
FIG. 6 is an optical diagram of the measuring system of the embodiment of the present invention.

As illustrated in FIG. 6, the measuring optical system 51 consist of: an X direction detection system 56 comprising a half mirror 15, a mirror 16, a relay lens 17, a mirror 18, a chopper 19, a condenser lens 20, and a light receiving element 21; a Y direction detection system 57 comprising the half mirror 15, a mirror 22, a relay lens 23, the chopper 19, a condenser lens 24, and a light receiving element 25; and a reference signal generation means 58 comprising a light emitting element 26, condenser lenses 27, 28, and a light receiving element 29. The chopper 19 has a group of slits that are continuous in the circumferential direction and rotates about the optical axis.

Figure 7:
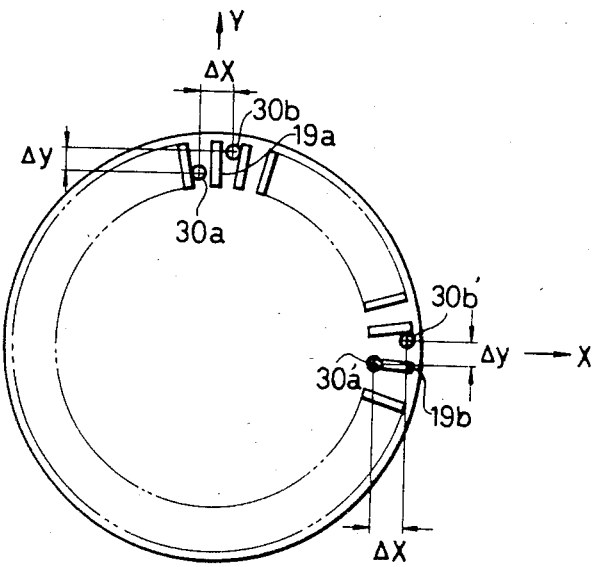
FIG. 7 is a schematic view useful for explaining the principle of measurement of the measuring system shown in FIG. 6.

In the abovementioned construction, the measuring target image on the eye fundus $P_2$ of the patient's eye is projected close the upper portion 19a of the chopper 19 by the light receiving optical system 52 and the X direction detection system 56. At the same time, the measuring target image of the eye fundus $P_2$ of the patient's eye is projected close to the side portion 19b of the chopper 19 by the target light receiving optical system 52 and the Y direction detection system 57. When the measuring target 5 and the eye fundus $P_2$ of the patient's eye do not have the conjugate relation, the round aperture images 30a and 30b (30a' and 30b') formed by the rays of light from the infrared light sources 1a and 1b are projected to the slit group while being separated by $\Delta x$ and $\Delta y$ in both the X and Y directions, as shown in FIG. 7.

In the abovementioned construction, $\Delta x$ is calculated from the phase difference between a signal from the light receiving element 21 when the infrared light source 1a is lit and the round aperture image 30a by its light is scanned by the chopper 19, and a signal from the light receiving element 21 when the infrared light source 1b is lit and the round aperture image 30b by its light is scanned by the chopper 19. Similarly, $\Delta y$ is calculated from the phase difference of the signal from the light receiving element 25 when the round aperture images 30a' and 30b' are scanned by the chopper 19. Here, explanation will be made only of the conjugate relation between the measuring target 5 and the eye fundus $P_2$ of the patient's eye and the relation between the cylindrical power of the patient's eye E and the round aperture images 30a, 30b on the chopper 19. It will be assumed that the light sources 1a and 1b are disposed in alignment with each other at a position rotated by an angle $\theta$ from the vertical direction. In other words, it will be assumed that the meridian direction being measured is one that is rotated by $\theta$ from the vertical direction.

Figure 8A:
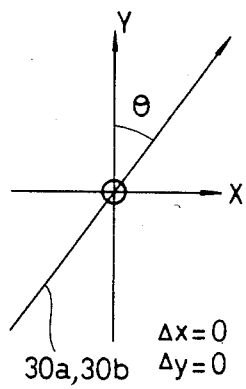
FIGS. 8(a–c) are also schematic views useful for explaining the principle of measurement of the measuring optical system.

(1) When the measuring target 5 and the eye fundus $P_2$ of the subject eye have the conjugate relation and if the patient's eye does not have cylindrical power, the round aperture images 30a and 30b are projected superposed on the optical axis passing position on the chopper, as shown in FIG. 8A. In other words, $\Delta x = \Delta y = 0$.

Figure 8B:
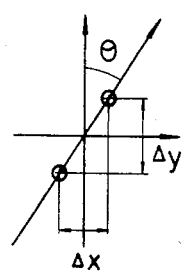

(2) When the measuring target 5 and the eye fundus $P_2$ of the patient's eye do not have the conjugate relation and the patient's eye E does not have cylindrical power, or if the main meridian line of the patient's eye E is in agreement with the measuring meridian direction by the light sources 1a and 1b when the patient's eye E has cylindrical power, the round aperture images 30a and 30b are projected separately in the measuring meridian direction on the chopper 19, as shown in FIG. 8B.

Figure 8C:
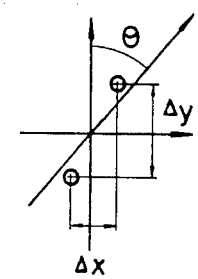

(3) If the measuring target 5 and the patient's eye fundus $P_2$ do not have the conjugate relation, the patient's eye E has cylindrical power and the main meridian direction of the patient's eye E is different from the measuring meridian direction by the light sources 1a and 1b, the round aperture images 30a and 30b are separately projected on the chopper 19 in the measuring meridian direction and the direction orthogonal to it, as shown in FIG. 8C.

In this embodiment, the amounts of separation Δx and Δy in the horizontal and vertical directions are detected as shown in FIG. 8 and are converted into the amount of separation in the measuring meridian direction from the results of the detection in order to detect the refraction in the measuring meridian direction.

Since the abovementioned conversion is effected, the refraction in each measuring meridian direction can be determined by simply rotating the light sources 1a and 1b.

As shown in FIG. 4, the fixed reference target system 53 consists of a visible light source 31, a condenser lens 32, a fixed reference target 33 movable in the direction of the optical axis, a mirror 34, a projection lens 35, and a dichroic mirror 36 reflecting the visible light but transmitting the infrared light.

In the abovementioned construction, the rays of light from the visible light source 31 illuminate the fixed reference target 33 via the condenser lens 32. The rays of light from the fixed reference target 33 are projected into the patient's eye E through the mirror 34, the projection lens 35, the dichroic mirror 36 and further through the aforementioned dichroic mirror 9. The subject fixes his visual direction by gazing at the fixed reference target 33. It is necessary that the patient's eye should always be in a state of far vision. The fixed reference target 33 is movable in the direction of the optical axis and is adjusted to a position where the patient's eye attains the far vision.

Figure 9:
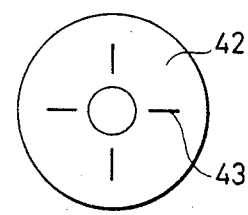
FIG. 9 is a front view of the fixed reference target in the embodiment of the present invention.

The illumination optical system 54 consists of a half mirror 9, a dichroic mirror 36, a projection lens 36', a half mirror 37 and an image pickup tube 38 that are arranged on the same optical axis, a light source 40, a condenser lens 41, a sight target 42, a mirror 44 and a projection lens 45 that are arranged on the optical axis of the light reflected from the half mirror 37. The image pickup tube 38 is connected to a monitor television 39. As shown in FIG. 9, the sight target 42 has a sight scale 43 having a circle at the center and radial lines around the circle.

In the illumination optical system having the abovementioned construction, a front eye image of the patient's eye E by the projection lens 36' and the image of the sight scale 43 by the projection lens 45 are projected in superposition on the image pickup tube 38. The inspector moves the apparatus of the present invention up and down and to the right and left while viewing the monitor television 39 until the center of the pupil image of the patient's eye is in agreement with the image of the sight scale 43 and the optical axis of the patient's eye is in agreement with the optical axis of the target projecting optical system 50 and the optical axis of the target light receiving optical system 52.

The construction of the electric circuit of the present apparatus will now be explained with reference to the block diagram shown in FIG. 10. A control circuit 101 is connected to each of the power switch 102, a measuring switch 103, chopper driving circuit 104, light source driving circuit 105, measuring target driving circuit 106, fixed reference target driving circuit 107, measuring target light source rotation driving circuit 108, measuring detecting portion 109 and operation processing portion 110 and controls these circuit elements in accordance with a predetermined program.

The chopper driving circuit 104 is connected to a motor 112 for rotating the chopper 19 and drives the same. The light source driving circuit 105 is connected to a reference signal light emitting element 26 and to the measuring target light sources 1a, 1b and lights them. The measuring target driving circuit 106 is connected to a motor 114 for moving the measuring target on the optical axis and drives the same. The fixed reference target driving circuit 107 is connected to a motor 116 for moving the fixed reference target on the optical axis and drives the same. The measuring target light source rotation driving circuit 108 is connected to a motor 118 for rotating and driving the light sources 1a, 1b and the condenser lenses 2a, 2b about the optical axis, and rotates and drives the same. The light receiving element 29 receives the light emitted by the reference signal light emitting source 26 and passed through the chopper 19, and applies the light to an amplification circuit 120. The amplification circuit 120 is connected to a waveform shaping circuit 122, which is in turn connected to a first phase difference detection circuit 124 and to a second phase differance detection circuit 126. The light receiving element 21, which receives the light emitted from the measuring target light sources 1a, 1b and passing through the upper portion 19a of the chopper 19, is connected to an amplification circuit 127, which is connected to an AGC circuit 128. The AGC circuit 128 is connected to a waveform shaping circuit 130, which is in turn connected to the first phase difference detection circuit 124.

Similarly, the light receiving element 25, that receives the light emitted from the measuring target light sources 1a, 1b and passed through the side portion 19b of the chopper 19, is connected to an amplification circuit 132, which is in turn connected to an AGC circuit 134. The AGC circuit 134 is connected to a waveform shaping circuit 136, which is in turn connected to the second phase difference detection circuit 126. The first phase difference detection circuit 124 detects the phase difference between the reference square wave generated from the waveform shaping circuit 122 and the square wave generated from the waveform shaping circuit 130 and produces a phase difference signal Xa. Similarly, the second phase difference detection circuit 126 detects the phase difference between the reference square wave generated by the waveform shaping circuit 122 and the square wave generated from the waveform shaping circuit 136, and produces a phase difference signal Ya. The first and second phase difference detection circuits 124 and 126 are connected to a comparison circuit 138, which is connected to the operation processing portion 110.

The comparison circuit 138 calculates the phase difference ΔX between the phase difference signals Xa and Xb generated by the first phase difference detection circuit 124 when the light emitting elements 1a and 1b are lit, and the phase difference ΔY between the phase difference signals Ya and Yb generated by the second phase difference detection circuit 126 when the light emitting elements 1a and 1b are lit.

These phase differences ΔX and ΔY correspond to the amount of separation Δx and Δy in the X and Y directions of the round aperture images 30a and 30b in FIG. 8. Using the following equation (5), the operation processing portion 110 calculates the phase difference $\Delta p\theta_i$ which corresponds to the amount of separation in the measuring meridian direction, from the angle $\theta_i$ of rotation of the position of the measuring target light source as a signal from the target light source driving circuit and from the abovementioned phase differences $\Delta x_i$ and $\Delta y_i$:

$$\Delta p\theta_i \Delta Xi \cos\theta + \Delta Yi \sin\theta_i \quad (5)$$

This phase difference $\Delta p\theta_i$ is converted into the amount of separation $\Delta$ of the round aperture image in the measuring meridian direction and the refraction $D\theta$ of the patient's eye in the measuring meridian direction in accordance with equation (4) on the basis of the aforementioned principle of calculating the refraction from this amount of separation $\Delta$. In the real measurement, $D\theta$ ($D\theta_1$, $D\theta_2$, $D\theta_3$) is calculated in at least three meridian directions. These $D\theta_1$, $D\theta_2$ and $D\theta_3$ can be expressed by the following equation (6) where A is the spherical power, B is the cylindrical power and $\alpha$ is the cylindrical axis:

$$\left. \begin{array}{l} D\theta_1 = A + B \cos 2(\theta_1 - \alpha) \\ D\theta_2 = A + B \cos 2(\theta_2 - \alpha) \\ D\theta_3 = A + B \cos 2(\theta_3 - \alpha) \end{array} \right\} \quad (6)$$

The spherical power, the cylindrical power and the cylindrical axis are determined and are then applied to the display 142.

In the abovementioned method, the spherical power A, the cylindrical power B and the cylindrical axis $\alpha$ are calculated only from the phase difference $\Delta p\theta_i$ corresponding to the amount of separation in the measuring meridian direction, but the following method is effective in determining the cylindrical power B and the cylindrical axis $\alpha$. Namely, the phase difference $\Delta P\theta_i$ corresponding to the amount of separation in the direction at right angles to the measuring meridian direction is calculated in accordance with the following equation (7), separately from the calculation of the phase difference $\Delta p\theta_i$ corresponding to the amount of separation in the measuring meridian direction from the phase differences $\Delta Xi$ and $\Delta Yi$ in accordance with equation (5):

$$\Delta P\perp i = -\Delta X \sin\theta_i + \Delta Yi \cos\theta_i \quad (7)$$

$\Delta P\perp i$ thus calculated can be expressed by the following equation (8) in the same way as equation (6):

$$\left. \begin{array}{l} \Delta P\perp 1 = B \cos 2(\theta_1 - \alpha) \\ \Delta P\perp 2 = B \cos 2(\theta_2 - \alpha) \\ \Delta P\perp 3 = B \cos 2(\theta_3 - \alpha) \end{array} \right\} \quad (8)$$

In other words, $\Delta P\perp i$ calculated in this manner is not affected by the cylindrical power A. This means that $\Delta P\perp i$ is not affected by the adjustment of the patient's eye during measurement, that is to say, it is not affected by the change in the cylindrical power A. From equation (8), the cylindrical power B and the cylindrical axis $\alpha$ can be detected with a high level of accuracy without being affected by the measurement of the subject during measurement. In this case, too, cylindrical power A can likewise be calculated using equations (5) and (6).

The electric circuit having the abovementioned construction operates in the following manner. After the power switch 102 is turned on, the optical axis of the subject is brought into agreement with the optical axes of the target projection optical system 50 and target light receiving optical system 52 using the illumination optical system 54. The chopper 19 is rotated by the control circuit 101, the reference light emitting element 26 is lit and the light sources 1a and 1b of the target projection optical system are alternately lit. The rotation and lighting are continued until the measurement is completed. Subject to control by the control circuit 101, the measuring target driving circuit 106 drives the motor 114 and moves the measuring target 5 to a predetermined position such as +6 diopter position, for example, while the fixed reference target driving circuit 107 drives the motor 116 so that the fixed reference target 23 is moved to a predetermined position such as +20 diopter, for example. Furthermore, the measuring target light source rotation driving circuit 108 drives the motor 118 so that the aligning direction of the light sources 1a and 1b of the measuring target 5 is rotated to the vertical direction (angle of rotation $\theta=0°$). In this manner, preparation of the pre-measurement is completed.

Next, as controlled by the control circuit 101, the light receiving elements 21, 25 and 29 receive the respective signal light beams and the operation processing portion 110 calculates the phase difference $\Delta p\theta o$ corresponding to the amount of separation of the round aperture image on the meridian plane ($\theta=0°$). This $\Delta p\theta o$ is converted to the amount of separation of the round aperture image and the refraction of the patient's eye on the meridian plane ($\theta=0°$) is calculated from the position of the measuring target 5 at this time. The result of this calculation is converted to amount of movement of the measuring target 5 and is applied to the control circuit 101. Upon receiving this signal, the control circuit 101 controls the measuring target driving circuit 106 and moves it away from the measuring target 5 until it is placed by the motor 114 at a position corresponding to the refraction of the patient's eye in the measuring meridian direction at $\theta=0°$, that is to say, a position where the measuring target 5 and the eye fundus of the patient's eye have a substantially conjugate relationship. In this state, the measuring target 5 and the fixed reference target 23 are fixed and the following real measurement is then effected. The position of the measuring target 5, which has been moved and fixed as a result of the pre-measurement, is kept unchanged during the real measurement.

The pre-measurement described above sets the measuring target 5 at a position which is substantially conjugate with the eye fundus of the patient's eye and is therefore effective in further improving the accuracy of the real measurement to be next described.

In the real measurement, the same detecting operation as in the pre-measurement is similarly effected. In the real measurement, the measuring target light source rotation driving circuit 108 receives a signal from the control circuit 101 and drives the motor 118 so that the light sources 1a and 1b of the measuring target are sequentially rotated about the optical axis and the refraction $D\theta$ of the patient's eye in the measuring meridian direction is calculated. This measurement is effected in at least three meridian directions and is expressed by the aforementioned equation (6) with $D\theta_1$, $D\theta_2$ and $D\theta_3$ representing the refraction in each direction. The spherical power A, the cylindrical power B and cylindrical axes $\alpha$ are calculated from the results and are finally displayed by the display 142. The greater the number of measuring meridian directions, the higher the measuring accuracy. A, B and $\alpha$ are calculated by the method of least squares. Though the pre-measurement is effected in only one meridian direction in this embodiment, it may of course be effected in three meridian directions. It is also possible to first perform pre-measurement in one meridian direction and to then perform the pre-measurement again in three meridian directions to improve the accuracy of the real measurement. Though the pre-measurement is effected prior to the real measurement in this embodiment, the present invention can be effectively practised and can provide the contemplated effects even when real measurement is carried out directly without performing the pre-measurement.

The invention has thus been shown and described with reference to a specific embodiment, however, it should be noted that the invention is in no way limited to the details of the illustrated arrangements but changes and modifications may be made without departing from the scope of the appended claims.

What is claimed is:

1. An eye refractometer comprising:
   a measuring target projection optical system for projecting first measuring target images from a pair of beams of light from a measuring target along an optical axis to the eye fundus of a patient's eye;
   a measuring target image-forming optical system for forming, on a plane perpendicular to the optical axis, second measuring target images of said beams of light projected from said measuring target to the eye fundus;
   detection means for detecting the positions of second target images formed on said plane;
   a target position control system for moving said target to a position along the optical axis substantially conjugate with the eye fundus of the patient's eye in the predetermined measuring direction in accordance with signals from said detection means, and for fixing the target at said position along the optical axis;
   rotation means for rotating said pair of beams of light around the optical axis while the target is fixed at said position along the optical axis; and
   refractive power calculating means for (1) calculating the refractive powers in at least three meridian directions from signals produced by said detecting means in response to the amount of separation of the two images in the measured meridian direction when the beams of light from said target fixed in said position are rotated around the optical axis, and for (2) calculating spherical power, cylindrical power, and the direction of the cylindrical axis from said signals.

2. The eye refractomer as defined in claim 1 wherein said measuring target projection optical system includes light source means comprised of a pair of light sources disposed symmetrically about the optical axis and alternately lightable at a high frequency.

3. The eye refractometer as defined in claim 1 wherein said measuring target image-forming optical system includes an objective lens system for condensing the beams of light reflected by the eye fundus, an aperture disposed behind said objective lens system at a position conjugate to the pupil of the patient's eye, and an image-forming lens for forming the second measuring target images from the beams of light transmitted through said aperture, said aperture being positioned forward of said image-forming lens.

4. The eye refractometer as defined in claim 1 wherein said measuring target image-forming optical system includes a light beam dividing member for dividing the beams of light and said detection means include a scanning member for scanning the two beams of light thus divided by said light beam dividing member in a plane perpendicular to the optical axis and two light receiving means disposed at the back of said scanning member in order to receive the beams of light transmitted through said scanning member.

5. The eye refractometer as defined in claim 4 wherein said scanning member is a rotary disc having groups of slits wherein the slits are each parallel to the radius of the disc.

6. The eye refractometer as defined in claim 4 wherein said two light receiving means are disposed a plane parallel to the plane of rotation of said rotary disc and define an angle of 90° with respect to the axis of rotation of said rotary disc.

* * * * *